United States Patent
Jasys et al.

[11] Patent Number: 6,057,364
[45] Date of Patent: May 2, 2000

[54] FLUORO-SUBSTITUTED ADAMANTANE DERIVATIVES

[75] Inventors: Vytautas John Jasys, Griswold; Robert A. Volkmann, Mystic, both of Conn.

[73] Assignee: Pfizer Inc, New York, N.Y.

[21] Appl. No.: 09/057,694

[22] Filed: Apr. 9, 1998

Related U.S. Application Data

[60] Provisional application No. 60/044,658, Apr. 10, 1997.

[51] Int. Cl.[7] .......................... C07C 61/12; C07C 233/01; C07C 233/58; C07C 211/34
[52] U.S. Cl. .......................................................... 514/511
[58] Field of Search .............................. 560/116; 562/498; 564/188, 457, 458, 454, 456; 514/511, 557, 623, 661; 544/238

[56] References Cited

U.S. PATENT DOCUMENTS

| | | | |
|---|---|---|---|
| 2,937,211 | 5/1960 | Ludwig | 260/666 |
| 3,391,142 | 7/1968 | Mills | 260/268 |
| 4,030,994 | 6/1977 | Kolloitsch | 204/159.11 |
| 4,578,382 | 3/1986 | Jarreau | 514/245 |
| 4,661,512 | 4/1987 | Laruelle | 514/423 |
| 4,829,086 | 5/1989 | Bodor | 514/542 |
| 5,098,895 | 3/1992 | Shroot | 514/62 |
| 5,212,303 | 5/1993 | Shroot | 544/69 |
| 5,480,905 | 1/1996 | Koda | 514/452 |
| 5,482,940 | 1/1996 | Abou-Gharbia | 514/252 |
| 5,599,998 | 2/1997 | Kraus | 564/455 |

FOREIGN PATENT DOCUMENTS 1069563  5/1967  United Kingdom .

OTHER PUBLICATIONS

Koch et al., Anodic Acetamid . . . 1–Haloadamantanes, Tetrahedron Letters, No. 9, pp. 693–696, Feb. 1973.

Koch et al., Anodic . . . Substituents, J. of the American Chem. Soc., vol. 95, No. 26., pp. 8631–8637, Dec. 1973.

Sorochinskii et al., Fluorine . . . Adamantane, Zh. Org. Khim. vol. 15, No. 12, pp. 2480–2484, No Month Provided 1979.

Fridman et al., Synthesis . . . Adamantane Derivatives, Khim.–Farm. Zh., vol. 13, No. 12, pp. 24–31, No Month Provided 1979.

Silverman, The Organic Chemistry of Drug Design and Drug Action, pp. 15–22, No Month Provided 1992.

Lewis, Sr., Hawley's Condensed Chemical Dictionary, Twelfth edition, p. 49, No Month Provided 1993.

Adcock et al., Transmission of . . . Adamant–1–yl Fluorides, J. Org. Chem., vol. 52, No. 3, pp. 356–364, Feb. 1987.

Rozen et al., Direct Synthesis of Fluoro . . . Fluorine, J. Org. Chem., vol. 53, No. 12, pp. 2803–2807, 1988.

Anderson et al., 1998, Synth. Comm. 18:1967–1974, "Novel synthesis of 3–fluoro–1–aminoadamantane and some of its derivatives".

Anderson et al., 1989, Synth. Comm. 19:1955–1963, "Novel synthesis of some 1–N–(3–fluoroadamantyl) ureas".

Sorochinskiy et al., 1979, J. Org. Chem. XV:2480–2484, "Fluorine derivatives of adamantane, VII. Fluorination of amine derivatives of sulfur tetrafluoride adamantane in the presence of hydrogen fluoride" (with English translation).

Tsuzuki et al., 1991, Biochem. Pharmacol. 41:R5–R8, "Adamantane as a brain–directed drug carrier for poorly absorbed drugs".

*Primary Examiner*—Rosalynd Keys
*Attorney, Agent, or Firm*—Peter C. Richardson; Paul H. Ginsburg; Alan L. Koller

[57] ABSTRACT

The invention relates to fluoro-substituted adamantane derivatives of the formula

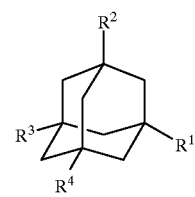

I and to pharmaceutically acceptable salts thereof, wherein $R^1$, $R^2$, $R^3$, and $R^4$ are as defined herein. The invention also relates to methods of treating neurological disorders, such as memory loss and Parkinson's disease, and bacterial and viral infections, through administration of a therapeutically effective amount of a compound of formula I. The invention also relates to a method of increasing the metabolic stability of an adamantane-containing pharmaceutical compound by incorporating a fluoro substituent on at least one bridge-head carbon of the adamantyl group of said adamantane-containing pharmaceutical compound

11 Claims, No Drawings

FLUORO-SUBSTITUTED ADAMANTANE DERIVATIVES

This application claims priority under 35 U.S.C. §119(e) from U.S. provisional application 60/044,658, filed Apr. 10, 1997.

BACKGROUND OF THE INVENTION

The present invention relates to fluoro-substituted adamantane derivatives that are metabolically more stable than the corresponding adamantane derivatives that are not fluoro-substituted. To enhance the metabolic stability of a pharmaceutical compound that includes an adamantane moiety, in accord with the present invention a fluoro-substituted adamantane moiety may be introduced in the pharmaceutically active compound in place of the non-fluorinated adamantane moiety. The fluoro-substituted adamantane derivatives of the present invention may also be used as pharmaceutical compounds for the treatment or prevention of memory loss, or for the treatment of Parkinson's disease or viral infections.

The addition of an adamantane moiety to the chemical structure of a pharmaceutical compound is a recognized method of enhancing the absorption of the compound in the central nervous system (CNS) of a patient. J. Pharmaceutical Sciences 83, 481 (1994). Since this property may be beneficial for pharmaceutical compounds directed to the CNS, efforts have been made to modify existing drugs to include the adamantane functionality. Biochem. Pharmacol. 41(4), R5–R8 (1991). Several adamantane-containing pharmaceutical compounds have been developed, including the following: amantadine hydrochloride (antiviral agent; treatment of Parkinson's disease), tromantadine (antiviral agent), amantol (antifungal; antibacterial agent), adatanserin (anxiolytic agent), rimantadine (antiviral agent), memantine (memory enhancement agent), somantadine (antiviral agent), and adapalene (antiacne agent). The adamantane moiety is lipophilic, which facilitates the tissue distribution of a drug containing the moiety, but the lipophilic nature of the adamantane group may also facilitate the metabolic degradation of the adamantane group through oxidation. In accord with the present invention, it has been found that by fluorinating one or more of the bridge-head carbons of the adamantane group, the metabolic stability of the adamantane group is enhanced without affecting the lipophilicity of the group.

SUMMARY OF THE INVENTION

The present invention relates to compounds of the formula

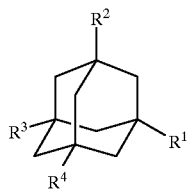

I and to pharmaceutically acceptable salts thereof, wherein:
$R^1$ is —NHC(O)$R^5$, —C(O)NH$R^5$, —(C$R^5R^6$)$_n$N$R^5R^6$ or —(C$R^5R^6$)$_n$CO$_2R^5$ wherein n is an integer ranging from 0 to 4;
$R^2$, $R^3$ and $R^4$ are each independently selected from the group consisting of H, fluoro, $C_1$–$C_4$ alkyl and hydroxy, provided at least one of $R^2$, $R^3$ and $R^4$ is fluoro;
each $R^5$ and $R^6$ is independently H or $C_1$–$C_4$ alkyl;
with the proviso that (1) when $R^1$ is —CO$_2$H, then $R^2$ is fluoro and $R^3$ and $R^4$ are not H, and (2) when $R^1$ is —NH$_2$, then $R^2$ is fluoro and $R^3$ is not H.

Specific embodiments of the compounds of formula I include those wherein $R^1$ is —CO$_2$H or —NH$_2$.

Other specific embodiments of the compounds of formula I include those wherein $R^2$, $R^3$, and $R^4$ are each fluoro.

Other specific embodiments include the following compounds:
Methyl-3-fluoro-5-hydroxyadamantane-1-carboxylate;
3,5-Difluoro-adamantan-1-ylamine;
Methyl-3,5-difluoro-7-hydroxyadamantane-1-carboxylate;
3,5,7-Trifluoroadamantane-1-carboxylic Acid;
3,5,7-Trifluoroadamantan-1-ylamine;
and the pharmaceutically acceptable salts of the foregoing compounds.

The invention also relates to a pharmaceutical composition for treating or preventing a neurological disorder, such as memory loss or Parkinson's disease, or a bacterial or viral infection, in a mammal, in particular a human, which comprises a therapeutically effective amount of a compound of formula I, or a pharmaceutically acceptable salt thereof, and a pharmaceutically acceptable carrier.

The invention also relates to a method of treating or preventing a neurological disorder, such as memory loss or Parkinson's disease, or a bacterial or viral infection, in a mammal, in particular a human, which comprises administering to said mammal a therapeutically effective amount of a compound of formula I or a pharmaceutically acceptable salt thereof.

The present invention also relates to a method of increasing the metabolic stability of a pharmaceutically active adamantane compound, which comprises including a fluoro substituent on at least one bridge-head carbon of the adamantyl group of said adamantane compound. In the foregoing method, the bridge-head carbons are the 1, 3, 5 and 7 carbons of the adamantyl group.

The term "pharmaceutically active adamantane compound", as used herein, unless otherwise indicated, includes any pharmaceutically active compound that has an adamantane moiety as part of its chemical structure, and pharmaceutically acceptable salts thereof. The term "pharmaceutically active adamantane compound" also includes pharmaceutically active compounds that form a salt with an adamantane derivative, such as the amantadine salt of N-acetyl-DL-phenylalanine. Examples of pharmaceutically active adamantane compounds include the following: amantadine, adatanserin, tromantadine, amantanium bromide, rimantadine, memantine, somantadine, adapalene, N-1-adamantyl-N'-cyclohexyl-4-morpholinecarboxamidine, dopamantine, adaprolol maleate, (–)-N-(2-(8-methyl-1,4-benzodioxan-2-ylmethylamino)ethyl) adamantane-1-carboxamide, N-(1-adamantyl)-N', N'-(1,5-(3-(4(5)-1 H-imidazolyl-pentanediyl))) formamidine, adamantoyl-Lys-Pro-Tyr-Ile-Leu, 1-(2-pyridyl)-4-(1-methyl-2-(1-adamantylamino) ethyl)piperazine, adafenoxate, (1 R,3S)-3-(1adamantyl)-1-aminomethyl-3,4-dihydro-5,6-dihydroxy-1 H-2-benzopyran, adamantylamide L-Ala-L-isoGlu, 2-adamantylamino-benzoic acid, N(alpha)-(1-adamantanesulphonyl)-N-(4-carboxybenzoyl)-L-lysyl-alanyl-L-valinal, 4-acylamino-1-aza-adamantane, L-leucyl-D-methionyl-glucyl-N-(2-adamantyl)-L-phenylalanylamide, Tyr-(D)-Met-Gly-Phe-adamantane, 1-N-(p-bromobenzoyl)methyladamantylamine, 4-butyl-1,2- dihydro-5-((1-adamantanecarbonyl)oxy) -1,2-diphenyl-3H-pyrazol-3-one, N(alpha)-(1-adamantanesulphonyl)-N(epsilon)-succinyl-L-lysyl-L-prolyl-L-valinal, and the amantadine salt of N-acetyl-DL-phenylalanine.

The foregoing pharmaceutically active adamantane compounds find utility as antifungal agents, antiviral and antibacterial agents, membrane permeability enhancers, anxiolytic agents, antidepressants, memory enhancers, antiacne agents, anti-inflammatory agents, analgesics, antihistamines, antihypertensives, antiglaucoma agents, and antiarrhythmic agents. The foregoing adamantane compounds may also find utility in the treatment of Parkinson's disease, psoriasis and emphysema.

The term "alkyl", as used herein, unless otherwise indicated, includes saturated monovalent hydrocarbon radicals having straight, cyclic or branched moieties, or combinations thereof. It is understood that for cyclic moieties at least three carbon atoms are required in said alkyl group.

The phrase "pharmaceutically acceptable salt(s)", as used herein, unless otherwise indicated, includes salts of acidic or basic groups which may be present in the compounds of formula I. The compounds of formula I that are basic in nature are capable of forming a wide variety of salts with various inorganic and organic acids. The acids that may be used to prepare pharmaceutically acceptable acid addition salts of such basic compounds of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e. 1 1'-methylene-bis-(2-hydroxy-3-naphthoate)] salts. The compounds of formula I that include an amino moiety may form pharmaceutically acceptable salts with various amino acids, in addition to the acids mentioned above.

Those compounds of the formula I that are acidic in nature are capable of forming base salts with various pharmacologically acceptable cations. Examples of such salts include the alkali metal or alkaline earth metal salts and, particularly, the calcium, magnesium, sodium and potassium salts of the compounds of formula I.

Certain compounds of formula I may have asymmetric centers and therefore exist in different enantiomeric and diastereomic forms. This invention relates to the use of all optical isomers and stereoisomers of the compounds of formula I, and mixtures thereof, and to all pharmaceutical compositions, methods of treatment, and methods of increasing the metabolic stability of adamantane-containing pharmaceutical compounds, as defined above, that may employ or contain them.

The present invention includes the compounds of formula I, and the pharmaceutically acceptable salts thereof, wherein one or more hydrogen, carbon or other atoms are replaced by isotopes thereof. Such compounds may be useful as research and diagnostic tools in metabolism pharmacokinetic studies and in binding assays.

Detailed Description Of The Invention

The preparation of the compounds of the present invention is illustrated in the following Scheme. Unless otherwise indicated, $R^1$, $R^2$, $R^3$, and $R^4$ in the reaction Scheme and discussion that follows are as defined above.

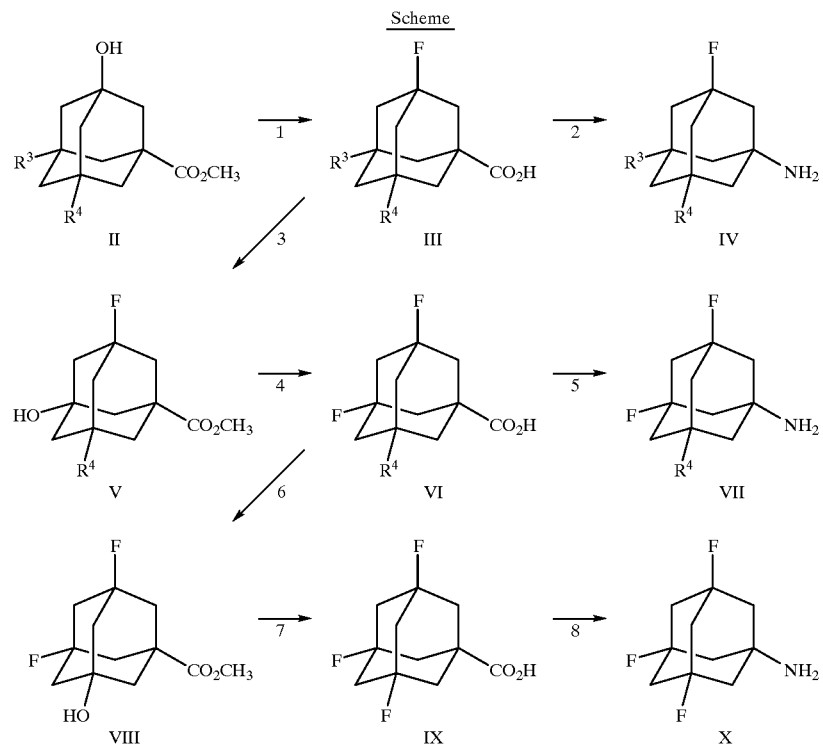

The compounds of the present invention are readily prepared. In the Scheme referred to above, the starting compound of formula II may be prepared according to methods known to those skilled in the art. Such methods are referred to in several published or issued patents including U.S. Pats. Nos. 2,937,211 (issued May 17, 1960) and 3,352,912 (issued Nov. 14, 1967), and United Kingdom patent 1,069,563 (published May 17, 1967). The alcohol of formula II may be converted to the corresponding fluoro-substituted compound of formula III by first treating the compound of formula II with diethylaminosulfur trifluoride (DAST) in a solvent such as dichloromethane at a temperature ranging from ambient temperature (20–25° C.) to reflux to provide the corresponding fluoro-substituted ester. The fluoro-substituted ester can be converted to the acid of formula III by hydrolyzing the ester according to methods known to those skilled in the art, such as by base-catalyzed hydrolysis. The acid of formula III can be converted to the corresponding amine of formula IV by first treating the acid of formula III with triethylamine, diphenylphosphoryl azide, and benzyl alcohol, and heating the reaction mixture to reflux to provide the corresponding benzyl carbamate intermediate which may be converted to the amine of formula IV by catalytically hydrogenating the benzyl carbamate intermediate.

The amine of formula IV includes a single fluoro group at a bridge-head carbon of the adamantane group. To add a second fluoro group to another bridge-head carbon of the adamantane group, the acid of formula III (wherein $R^3$ is H) may be converted to the compound of formula V. In step 3 of the Scheme, the acid of formula III may be hydroxylated by treating the compound of formula III with potassium hydroxide and potassium permanganate. The resulting compound may be further treated with an aqueous solution containing tetrabutylammonium hydrogen sulfate and sodium bicarbonate to provide the salt of the acid moiety followed by treatment with methyl iodide to provide the ester of formula V. The ester of formula V may be converted to the acid of formula VI according to the procedure described above for step 1 of the Scheme. The acid of formula VI may be converted to the amine of formula VII according to the procedure described above for step 2 of the Scheme.

To add a third fluoro group to a bridge-head carbon of the adamantane moiety, the acid of formula VI (wherein $R^4$ is H) may be hydroxylated and esterified as described above for step 3 of the Scheme. Further, the ester of formula VIII may be converted to the corresponding fluoro-substituted acid of formula IX as described above for step 1 of the Scheme. The acid of formula IX can be converted to the corresponding amine of formula X as described above for step 2 of the Scheme.

The compounds specifically exemplified in the Scheme above may be converted to other compounds of formula I, or introduced into an adamantane-containing pharmaceutical compound to replace a non-fluorinated adamantane group, according to various methods known to those skilled in the art. In particular, the acid moiety of the acids of formulas III, VI and IX may be esterified according to methods known to those skilled in the art. The amine moiety of the amines of formulas IV, VII and X may be acylated or alkylated to provide secondary and tertiary amines and amides. Methods of modifying the compounds of formula I and the compounds specifically referred to in the Scheme above are referred to in several issued patents including U.S. Pats. Nos. 2,937,211 and 3,352,912, and United Kingdom patent 1,069,563, each of which is referred to above, as well as the following U.S. Pats. Nos.: 3,391,142 (issued Jul. 2, 1968); 3,152,180 (issued Oct. 6, 1964); 3,705,194 (issued Dec. 5, 1972); 4,288,609 (issued Sep. 8, 1981); 4,476,319 (issued Oct. 9, 1984); 4,514,332 (issued Apr. 30, 1985); 4,578,382 (issued Mar. 25, 1986); 4,623,639 (issued Nov. 18, 1986); 4,661,512 (issued Apr. 28, 1987); 4,717,720 (i4,829,086 (issued Jan. 5, 1988); 4,829,086 (issued May 9, 1989); 5,098,895 (issued Mar. 24, 1992); 5,212,303 (issued May 18, 1993); 5,480,905 (issued Jan. 2, 1996); 5,482,940 (issued Jan. 9, 1996); and 5,599,998 (issued Feb. 4, 1997).

The compounds of the present invention may have asymmetric carbon atoms and therefore exist in different enantiomeric and diastereomic forms. Diastereomeric mixtures can be separated into their individual diastereomers on the basis of their physical chemical differences by methods known to those skilled in the art, for example, by chromatography or fractional crystallization. Enantiomers may be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered to be part of the present invention.

The compounds of formula I that are basic in nature are capable of forming a wide variety of different salts with various inorganic and organic acids, including amino acids. Although such salts must be pharmaceutically acceptable for administration to mammals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the formula I that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium, magnesium, various amine cations, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

Like the non-fluorinated adamantane-containing pharmaceutical compounds that are structurally related to the compounds of formula I, the compounds of formula I, and the pharmaceutically acceptable salts thereof, may be used to treat or prevent neurological disorders, such as memory loss and Parkinson's disease, as well as bacterial and viral infections, in a mammal, in particular a human. It is well known that non-fluorinated adamantane-containing pharmaceutical compounds related to the compounds of formula I include amantadine (1-aminoadamantane), somantadine (1-(2-amino-2-methyl)propyladamantane), and rimantadine (1-amino-(1-adamantane)ethane), each of which is useful as an antiviral agent, as well as memantine (3,5-dimethyl-1-adamantaneamine) which is also useful for the treatment of memory loss and Parkinson's disease. The activity of the compounds of formula I, and the pharmaceutically acceptable salts thereof, in the treatment or prevention of a neurological disorder, such as memory loss or Parkinson's disease, may be assessed in accord with one or more tests referred to in U.S. Pat. No. 4,476,319, referred to above. The activity of the compounds of formula I, and the pharmaceutically acceptable salts thereof, in the treatment of bacterial or viral infections may be assessed in accord with one or more tests referred to in U.S. Pat. No. 3,705,194, referred to above.

The compounds of formula I, and the pharmaceutically acceptable salts thereof (hereinafter "the active compounds"), may be administered through oral, parenteral, topical, or rectal routes. In general, these compounds are most desirably administered in dosages ranging from about 1 to about 300 mg per day, in single or divided doses (i.e., from 1 to 4 doses per day), although variations will necessarily occur depending upon the species, weight and condition of the subject being treated and the particular route of administration chosen. However, a dosage level that is in the range of about 0.1 mg to about 30 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like.

Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules, preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the active compounds of the present invention topically and this may be done by way of creams, jellies, gels, pastes, patches, ointments and the like, in accordance with standard pharmaceutical practice.

The metabolic stability of the active compounds may be assessed according to the following procedure. A standard microsomal incubation condition is prepared for assessing the rate of metabolism of the active compound in liver microsomes. The microsomal incubation condition comprises 100 mM potassium phosphate buffer (pH 7.4), 10 mM $MgCl_2$, 0.5 mM $NADP^+$(nicotinamide adenine dinucleotide phosphate) 4 mM glucose 6 phosphate, 10 unit/mL glucose 6 phosphate dehydrogenase, 0.2 $\mu$M microsomal cytochrome P450, and 10 $\mu$M active compound. The incubation is started by adding substrate to the reaction mixture that has been preincubated for approximately 3 minutes at 37° C. An aliquot is removed at 0, 1, 2, 5, 10, and 20 minute time points and added to an equal volume of methanol to quench the reaction. The precipitate in the samples is removed by centrifugation and the supernatants are stored at −20° C. The samples are analyzed by standard LC/MS to determine the amount of active compound that has been metabolically degraded.

TABLE

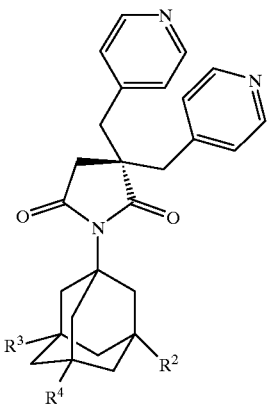

| % Loss (10 minutes) | R² | R³ | R⁴ |
|---|---|---|---|
| >75% | H | H | H |
| 75% | F | H | H |
| 75% | F | F | H |
| 10% | F | F | F |

The compounds illustrated in the chemical formula provided for the Table above were prepared as described in PCT published patent application WO 95/29909, which was published Nov. 9, 1995, entitled "Novel Acyclic And Cyclic Amides As Neurotransmitter Release Enhancers." The compounds illustrated above are pharmaceutically active compounds that enhance the release of neurotransmitters such as acetylcholine, dopamine and serotonin, and therefore are useful for treating Alzheimer's disease, age-associated memory impairment, Parkinson's disease and other central nervous system disorders in mammals, in particular humans. The metabolic stability of the above compounds was assessed according to the procedure described above. The metabolic stability of the above compounds is provided in the above table in the column marked "% Loss" which indicates the amount of compound that was metabolically degraded after 10 minutes in a standard microsomal incubation condition which was prepared as described above. As the table illustrates, those compounds in which the adamantane moiety is fluorinated, in particular the trifluoro species, are metabolically more stable than the corresponding compound in which the adamantane moiety is not fluorinated.

The Examples provided below illustrate specific embodiments of the invention. It will be understood that the invention is not limited to the specific details of these examples.

EXAMPLE 1

Fluoroadamantane-1-carboxylic Acid

Under a $N_2$ atmosphere was added 26.17 ml (0.20 ml) of diethylaminosulfur trifluoride (DAST) to 24 ml. of dry dichloromethane which was cooled to −78° C. To this solution was added drop-wise a dichloromethane solution (10 ml) of methyl 3-hydroxyadamantane-1-carboxylate (42.0 g, 0.20 mol). The suspension was allowed to warm to ambient temperature and stirred for 1 hour. To the resultant solution was added water (500 ml). The organic layer was separated, washed with brine, dried over magnesium sulfate, filtered and concentrated in vacuo to afford 41.6 g (98%) of crude product, mp <34° C, which slowly crystallized. $^1$H NMR (CDCl₃) 1.70–1.80 (m-6H), 2.20–2.35(m-3H), 2.50–2.60 (m-6H), 7.00–7.70 (m-5H) $^{13}$C NMR (CDCl₃) 30.84 (10.11), 34.79 (0.91), 37.56, 41.81 (17.73), 43.70 (20.15), 44.86 (10.16), 51.86, 92.13 (184.14). Under a $N_2$ atmosphere was added to crude ester (41.6 g, 0.196 mol), 100 ml of methanol, 75 ml of tetrahydrofuran (THF), 50 ml of water followed by 16.0 g (0.40 mol) of NaOH pellets. The solution was allowed to stir overnight. The organic solvents were removed under reduced pressure, water (200 ml) was added and the solution was acidified to a pH of 1.0 with 6N HCl. The resultant solids were filtered, washed with water and air dried to afford 37.0 g (95%) of 3-fluoroadamantane-1-carboxylic acid (mp 154–156° C). An analytical sample of the title compound was obtained following an EtOAc/hexane recrystallization. Crystals from the recrystallization were suitable for X-ray analysis. Anal. Calc'd for $C_{11}H_{15}O_2F$: C, 66.65; H, 7.63; F, 9.58; Found: C, 66.44; H, 7.72; F, 9.22.

EXAMPLE 2

3-Fluoroadamantan-1-ylamine

Under a $N_2$ atmosphere was added 7.65 g (38.6 mmol) of 3-fluoroadamantane-1-carboxylic acid to 150 ml of dry benzene. To this solution was added 5.37 ml (38.8 mmol) of triethylamine (TEA) followed by 8.31 ml (38.8 mmol) of diphenylphosphoryl azide. The reaction mixture was heated to reflux for 45 minutes, then cooled to ambient temperature at which point 5.37 ml (38.8 mmol) of benzyl alcohol was added. The resultant reaction mixture was allowed to reflux for 72 hours. The crude reaction mixture was allowed to cool, concentrated in vacuo and chromatographed on silica gel using 4:1 hexane:EtOAc to afford 9.3 g (79%) of 3-fluoroadamantan-1ylamine benzyl carbamate: $^1$H NMR (CDCl₃) 1.53 (2H, m), 1.75–1.95 (8H, m), 2.10 (2H, m), 2.33 (2H, bs), 4.76 (1H, bs), 5.03 (2H, bs), 7.33 (5H, m); $^{13}$C NMR (CDCl₃) 30.80 (10.19), 34.52 (1.81), 40.25, 41.48 (17.74), 46.57 (18.79), 53.80 (12.23), 66.07, 92.30 (184.30), 127.99, 128.43, 136.47, 154.14). The benzyl carbamate was dissolved in 100ml of HOAc and combined with 2 g of 10% Pd/C and hydrogenated (50 psi (345 kPa; 3.4 atmos)) for a period of 5 hours. The crude reaction mixture was filtered, the catalyst was washed with HOAc and the filtrate was concentrated in vacuo to afford 7.4 g (>100%) of crude title compound as its acetate salt.

EXAMPLE 3

Methyl-3-fluoro-5-hydroxyadamantane-1-carboxylate

To an aqueous solution (400 ml) containing potassium hydroxide (13.0 g; 0.20 mol) was added 34.76 g (0.22 mol) of potassium permanganate and the solution was warmed on a steam bath (about 50° C). To this solution was added portion-wise 39.8 g (0.20 mol) of 3-fluoroadamantane-l-carboxylic acid. After the addition was complete, the reaction mixture was allowed to warm to a gentle reflux and stirred until all the potassium permanganate was consumed (about 1.5 hours). The reaction mixture was then cooled and acidified with 6N HCl. Sodium bisulfite was added to remove $MnO_2$ and the white suspension was filtered and washed with water to yield recovered starting material (19.0 g). The aqueous filtrate was saturated with NaCl and extracted with 95:5 EtOAc:MeOH (4×350 ml). The organic extracts were dried over magnesium sulfate, filtered and concentrated in vacuo to afford 18.3 g (43%; 81% based on recovered 3-fluoroadamantan-1-carboxylic acid) of 3-fluoro-5-hydroxyadamantane-1-carboxylic acid. To an aqueous solution (250 ml) containing tetrabutylammonium hydrogen sulfate (42g, 0.124 mol) was added portion-wise sodium bicarbonate (41.0 g, 0.496 mol). This solution was allowed to stir for 20 minutes at which point 26.5 g (0.124 mol) of 3-fluoro-5-hydroxyadamantane-1-carboxylic acid was added portion-wise. The reaction mixture was allowed to stir for 30 minutes, was concentrated in vacuo to afford a viscous oil which was dissolved in acetone (300 ml) and mixed with methyl iodide (40 ml) and allowed to stir for 48 hours. The crude reaction mixture was filtered, concentrated in vacuo and triturated with $Et_2O$ to remove tetrabutylammonium iodide and the crude filtrate was concentrated in vacuo to afford 31 g of crude ester which was chromatographed on 800 g of silica gel using 2:1 hexane:ethyl acetate to afford 23.5 g (83%) of the title compound: mp 51.5–52.6°C.; $^1H$ NMR ($CDCl_3$) 1.60–1.70 (4H, m), 1.75–1.82 (4H, m), 1.88–1.92 (3H, M), 1.94–1.98 (2H, m), 2.42–2.50 (1H, m) 3.67 (3H, s). $^{13}C$ NMR ($CDCl_3$) 30.52 (10.33), 36.36, 40.35, 42.60 (20.38), 45.16, 45.42 (10.18), 49.44 (17.36), 51.94, 70.62 (12.53), 92.71 (186.33), 175.04; Anal. Calc'd for $C_{12}H_{17}O_3F$: C, 63.14; H, 7.51; N, F, 8.32; Found: C, 63.25; H, 7.38; F, 8.52.

EXAMPLE 4

3, 5-Difluoroadamantane-1-carboxylic Acid

Under a $N_2$ atmosphere was added 22.8 g (100 mmol) of methyl-3-fluoro-5-hydroxyadamantane-1-carboxylate to 400 ml of dry chloroform and the resultant solution was cooled to –50° C. To this solution was added drop-wise 13.1 ml (100 mmol) of DAST. The suspension was allowed to warm to ambient temperature and then heated to reflux for 1.5 hours. The resultant solution was cooled and treated with water (400 ml). The organic layer was separated, and the aqueous layer was washed again with chloroform (50 ml). The organic extracts were washed with brine, dried over magnesium sulfate, filtered and concentrated in vacuo to afford 23.2 g of crude product. Under a $N_2$ atmosphere was added to 75 ml of methanol, 50 ml of THF, 250 ml of water, 22.0 g (95.6 mmol) of methyl 3,5-difluoroadamantane-1-carboxylate generated in this step, followed by 8.0 g (200 mmol) of NaOH pellets. The solution was allowed to stir overnight. The aqueous solution was extracted with ethyl acetate. The aqueous layer was acidified to a pH of 1.0 with 1N HCl and the resultant solution was extracted with ethyl acetate (200 ml), and this organic extract was washed with water, brine, dried over magnesium sulfate, filtered and concentrated in vacuo to afford 19.8 g (96%) of 3,5-difluoroadamantane-1-carboxylic acid. An analytical sample of this compound was obtained following an EtOAc/Hexane recrystallization: mp 162–164° C.; $^1H$ NMR ($CDCl_3$) $^{3}C$ NMR (DMSO) 30.16, 35.67, 39.55, 42.09, 44.92, 46.92, 93.29. Crystals from the recrystallization were suitable for X-ray analysis. Anal. Calc'd for $C_{11}H_{14}O_2F_2$: C, 61.10; H, 6.53; F, 17.57; Found: C, 61.00; H, 6.57; F, 17.32.

EXAMPLE 5

3,5-Difluoro-adamantan-1ylamine

The procedure of Example 2 for the conversion of 3-fluoroadamantane-1-carboxylic acid to 3-fluoroadamantan-1ylamine was utilized. 4.32 g (20 mmol) of 3,5-difluoroadamantane-1-carboxylic acid provided after 96 hours crude product which was chromatographed on silica gel using 4:1 hexane:EtOAc to afford 4.7 g (73%) of benzyl carbamate: mp 71.9–72.9° C.; 1H NMR (CDCl3) 1.80–1.90 (7H, m), 2.02–2.25 (6H, m) 2.40–2.50 (1H, m), 4.84 (1H, bs),5.04 (2H, bs), 7.30–7.40 (5H, m); $^{13}C$ NMR ($CDCl_3$) 29.07, 38.98, 40.15, 45.54, 47.16, 54.25, 66.37, 92.24 (188.67), 128.09, 128.17, 128.52, 128.56, 136.26, 154.18. Anal. Calc'd for $C_{18}H_2NO_2F_2$: C, 67.27; H, 6.59; N, 4.36; F, 11.82; Found: C, 66.96; H, 6.54; N, 4.33; F, 11.71. Hydrogenation (HOAc/Pd/C/50 PSI) of 7.84 g (24.4 mmol) of this intermediate for a period of 5 hours provided 7.8 g (>100%) of 3, 5-difluoro-adamantan-1ylamine as its acetate salt.

EXAMPLE 6

Methyl-3.5-difluoro-7-hydroxyadamantane-1-carboxylate

The procedure utilized for the conversion of 3-fluoroadamantane-1-carboxylic acid to methyl-3-fluoro-5-hydroxyadamantane-1-carboxylate, as described above, was modified. Treatment of 3,5-difluoroadamantane-1-carboxylic acid (19.8 g, 91.6 mmol) with 17.37 g (110 mmol) of potassium permanganate and 5.95 g of potassium hydroxide in 200 ml of $H_2O$ afforded, after 18 hours of reflux and normal workup (ethyl acetate extraction), 18.9 g of white solids containing 3, 5-difluoro-7-hydroxyadamantane-1-carboxylic acid and starting acid. Esterification of this mixture using tetrabutylammonium hydrogen sulfate (30.51g, 0.090 mol), sodium bicarbonate (30.24 g, 0.36 mol), and methyl iodide (30 ml) as described above afforded 9.7 g of 3,5-difluoroadamantane-1-carboxylic acid as its methyl ester and 9.22 g of methyl-3,5-difluoro-7-hydroxyadamantane-1-carboxylate (title compound): mp 99.5–101° C.; $^{13}C$ NMR ($CDCl_3$) 41.97, 43.92, 44.58, 46.46, 48.65, 52.69, 70.86, 92.28 (192.37); Anal. Calc'd for $C_{12}H_{16}O_3F_2$: C, 58.53; H, 6.55; F, 15.43; Found: C, 58.51; H, 6.51; F, 15.17.

EXAMPLE 7

3,5,7-Trifluoroadamantane-1-carboxylic Acid

The procedure for the conversion of methyl-3-fluoro-5-hydroxyadamantane-1-carboxylate to 3,5-difluoroadamantane-1-carboxylic acid was modified. Treatment of methyl-3,5-difluoro-7-hydroxyadamantane-1-carboxylate (8.5g 34.5 mmol) with DAST (4.5 ml, 34.5 mmol) afforded, after 8 hours of reflux and standard workup, crude product which was purified on silica gel (2:1 hexane:EtOAc) to provide 5.02 g of methyl-3,5,7-trifluoroadamantane-1-carboxylate: mp 108.5–110-C; $^1H$ NMR ($CDCl_3$) 1.95–2.22 (12H, m), 3.72 (3H, s); $^{13}C$ NMR ($CDCl_3$) 41.80, 43.06, 46.23, 52.44, (1.57 (191.16), 173.20. Anal. Calc'd for $C_{12}H_{15}O_2F_3$: C, 58.06; H, 6.09; N, F, 22.96; Found: C, 58.37; H, 6.13; F, 22.89. This product was saponified to afford after workup 4.43 g (55%) of 3,5,7-trifluoroadamantane-1-carboxylic acid as a white solid: mp 198–199° C.; $^1H$ NMR ($CDCl_3$) 1.90–2.25; $^{13}C$ NMR ($CDCl_3$) 41.54, 43.03, 46.21, 91.49 (191.61), 179.35. An analytical sample of this compound was obtained following an EtOAc/hexane recrystallization. Suitable crystals for X-ray analysis were grown by slow evaporation from EtOAc/hexane. Anal. Calc'd for $C_{11}H_{13}O_2F_3$: C, 56.41; H, 5.59; N, F, 24.33. Found: C, 56.23; H, 5.42; F, 24.10.

EXAMPLE 8

3, 5, 7- Trifluoroadamantan-1-ylamine

The procedure utilized for the conversion of 3-fluoroadamantane-1-carboxylic acid to 3-fluoroadamantan-1ylamine was utilized as described above in Example 2. 4.00 g (17.1 mmol) of 3,5,7-trifluoroadamantane-1-carboxylic acid provided after 18 hours crude product which was chromatographed on silica gel using 4:1 hexane:EtOAc to afford 4.12 g (71%) of benzyl carbamate; mp 91.5–92.0° C.; $^1$H NMR (CDCl$_3$) δ2.02–2.23 (2H, m), 2.33 (2H, bs), 4.76 (1H, bs), 5.03 (2H, bs), 7.33 (5H, m); $^{13}$C NMR (CDCl$_3$) 44.68, 46.29, 52.09, 90.69 (189.96). Anal. Calc'd for $C_{18}H_{20}NO_2F_3$: C, 63.71; H, 5.94; N, 4.13; F, 16.79; Found: C, 63.80; H, 5.88; N, 4.15;F, 16.68. Hydrogenation (HOAc/Pd/C/ 50 psi) of 3.8 g(11.2 mmol) of this intermediate for a period of 5 hours provided 4.5 g (>100%) of 3, 5, 7-trifluoroadamantan-1-ylamine as its acetate salt.

What is claimed is:

1. A compound of the formula

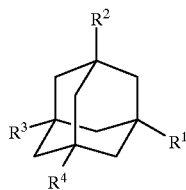

I or a pharmaceutically acceptable salt thereof, wherein:
R$^1$is —NHC(O)R$^5$, —C(O)NHR$^5$, —(CR$^5$R$^6$),NR$^5$R$^6$ or —(CR$^5$R$^6$)$_n$ CO$_2$R$^5$ wherein n is integer ranging from 0 to 4;
R2, R3 and R4 are each fluoro; and
each R$^5$ and R$^6$ is independently H or C$_1$–C$_4$ alkyl.

2. The compound of claim 1 wherein R$^1$is —CO$_2$H or —NH$_2$.

3. The compound of claim 1 selected from the group consisting of:
3,5,7-Trifluoroadamantane-1-carboxylic Acid;
3,5,7-Trifluoroadamantan-1-ylamine;
and the pharmaceutically acceptable salts of the foregoing compounds.

4. A pharmaceutical composition for treating or preventing a neurological disorder, or a bacterial or viral infection, in a mammal which comprises a therapeutically effective amount of a compound of claim 1 and a pharmaceutically acceptable carrier.

5. The pharmaceutical composition of claim 4 wherein said neurological disorder is memory loss or Parkinson's disease.

6. A method of treating or preventing a neurological disorder, or a bacterial or viral infection, in a mammal which comprises administering to said mammal a therapeutically effective amount of a compound of claim 1.

7. The method of claim 6 wherein said neurological disorder is memory loss or Parkinson's disease.

8. A method of increasing the metabolic stability of a pharmaceutically active adamantane compound which comprises including a fluoro substituent on three bridge-head carbons of the adamantyl group of said adamantane compound.

9. The method of claim 8 wherein said pharmaceutically active adamantane compound is selected from the group consisting of amantadine, adatanserin, tromantadine, amantanium bromide, rimantadine, memantine, somantadine, adapalene, N-1-adamantyl-N'-cyclohexyl-4-morpholinecarboxamidine, dopamantine, adaprolol maleate, (–)-N-(2-(8-methyl-1,4-benzodioxan-2-ylmethylamino) ethyl)adamantane-1-carboxamide, N-(1-adamantyl)-N',N'-(1,5-(3-(4(5)-1H-imidazolyl-pentanediyl)))formamidine, adamantoyl-Lys-Pro-Tyr-Ile-Leu, 1-(2-pyridyl)-4-(1-methyl-2-(1-adamantylamino)ethyl)piperazine, adafenoxate, (1R,3S)-3-(1'-adamantyl)-1-aminomethyl -3,4-dihydro-5,6-dihydroxy-1 H-2-benzopyran, adamantylamide L-Ala-L-isoGlu, 2-adamantylamino -benzoic acid, N(alpha)-(1-adamantanesulphonyl)-N-(4-carboxybenzoyl)-L -lysyl-alanyl-L-valinal, 4-acylamino-1-aza-adamantane, L-leucyl-D-methionyl-glucyl-N-(2-adamantyl)-L-phenylalanylamide, Tyr-(D)-Met-Gly-Phe-adamantane, 1-N-(p -bromobenzoyl)methyladamantyl amine, 4-butyl-1,2-dihydro-5-((1-adamantanecarbonyl) oxy)-1,2-diphenyl-3H-pyrazol-3-one, N(alpha)-(1-adamantanesulphonyl)-N(epsilon)-succinyl-L-lysyl-L -prolyl-L-valinal, and the amantadine salt of N-acetyl-DL-phenylalanine.

10. An adamantane compound selected from the group consisting of amantadine, adatanserin, tromantadine, amantanium bromide, rimantadine, memantine, somantadine, adapalene, N-1-adamantyl-N'-cyclohexyl-4-morpholinecarboxamidine, dopamantine, adaprolol maleate, (–)-N-(2-(8-methyl-1,4-benzodioxan-2-ylmethylamino) ethyl)adamantane-1-carboxamide, N-(1-adamantyl) -N',N'-(1,5-(3-(4(5)-1 H-imidazolyl-pentanediyl)))formamidine, adamantoyl-Lys-Pro-Tyr -Ile-Leu, 1-(2-pyridyl)-4-( 1-methyl-2-( 1-adamantylamino)ethyl)piperazine, adafenoxate, (1R,3S)-3-(1 '-adamantyl)-1-aminomethyl-3,4-dihydro-5,6-dihydroxy-1 H-2-benzopyran, adamantylamide L-Ala-L-isoGlu, 2-adamantylamino-benzoic acid, N(alpha)-(1-adamantanesulphonyl)-N-(4-carboxybenzoyl)-L-lysyl-alanyl-L-valinal, 4-acylamino-1-aza-adamantane, L-leucyl-D-methionyl-glucyl-N-(2-adamantyl)-L-phenylalanylamide, Tyr-(D)-Met-Gly-Phe-adamantane, 1-N-(p-bromobenzoyl)methyladamantyl amine, 4-butyl-1,2-dihydro-5-((1-adamantanecarbonyl)oxy)-1,2-diphenyl-3H-pyrazol-3-one, N(alpha)-(1-adamantanesulphonyl)-N (epsilon)-succinyl-L-lysyl-L-prolyl-L-valinal, and the amantadine salt of N-acetyl-DL-phenylalanine; which adamantane compound further comprises a fluoro substituent on three bridge-head carbons of the adamantyl group of said adamantane compound.

11. A pharmaceutical composition comprising a pharmaceutically acceptable carrier, and an adamantane compound selected from the group consisting of amantadine, adatanserin, tromantadine, amantanium bromide, rimantadine, memantine, somantadine, adapalene, N-1-adamantyl-N'-cyclohexyl-4-morpholinecarboxamidine, dopamantine, adaprolol maleate, (–)-N-(2-(8-methyl-1,4-benzodioxan-2-ylmethylamino)ethyl)adamantane-1-carboxamide, N-(1-adamantyl) -N',N'-(1,5-(3-(4(5)-1 H-imidazolyl-pentanediyl)))formamidine, adamantoyl-Lys-Pro-Tyr -Ile-Leu, 1-(2-pyridyl)-4-(1-methyl-2-(1-adamantylamino)ethyl)piperazine, adafenoxate, (1 R,3S)-3-(1 '-adamantyl)-1-aminomethyl-3,4-dihydro-5,6-dihydroxy-1 H-2-benzopyran, adamantylamide L-Ala-L-isoGlu, 2-adamantylamino-benzoic acid, N(alpha)-(1-adamantanesulphonyl)-N-(4-carboxybenzoyl)-L-lysyl-alanyl-L-valinal, 4-acylamino-1 aza-adamantane, L-leucyl-D-methionyl-glucyl-N-(2-adamantyl)-L-phenylalanylamide, Tyr-(D)-Met-Gly-Phe-adamantane, 1-N-(p-bromobenzoyl)methyladamantyl amine, 4-butyl-1,2-dihydro-5-((1-adamantanecarbonyl)oxy)-1,2-diphenyl-3H-pyrazol-3-one, N(alpha)-(1-adamantanesulphonyl)-N (epsilon)-succinyl-L-lysyl-L-prolyl-L-valinal, and the amantadine salt of N-acetyl-DL-phenylalanine, which adamantane compound further comprises a fluoro substituent on three bridge-head carbons of the adamantyl group of said adamantane compound.

* * * * *